United States Patent
Montgomery

(10) Patent No.: US 8,206,446 B1
(45) Date of Patent: Jun. 26, 2012

(54) METHOD FOR SURGICALLY REPAIRING A DAMAGED LIGAMENT

(75) Inventor: Kenneth D. Montgomery, Roslyn, NY (US)

(73) Assignee: Cayenne Medical, Inc., Scottsdale, AZ (US)

( * ) Notice: Subject to any disclaimer, the term of this patent is extended or adjusted under 35 U.S.C. 154(b) by 184 days.

(21) Appl. No.: 12/721,319

(22) Filed: Mar. 10, 2010

Related U.S. Application Data

(60) Provisional application No. 61/158,994, filed on Mar. 10, 2009, provisional application No. 61/158,999, filed on Mar. 10, 2009.

(51) Int. Cl.
*A61F 2/08* (2006.01)
(52) U.S. Cl. .................................................. 623/13.14
(58) Field of Classification Search ....... 623/13.11–13.2
See application file for complete search history.

(56) References Cited

U.S. PATENT DOCUMENTS

| | | |
|---|---|---|
| 3,708,883 A | 1/1973 | Flander |
| 3,832,931 A | 9/1974 | Talan |
| 4,311,421 A | 1/1982 | Okada et al. |
| 4,711,232 A | 12/1987 | Fischer et al. |
| 4,716,893 A | 1/1988 | Fischer et al. |
| 4,738,255 A | 4/1988 | Goble et al. |
| 4,744,793 A | 5/1988 | Parr et al. |
| 4,772,286 A | 9/1988 | Goble et al. |
| 4,778,468 A | 10/1988 | Hunt et al. |
| 4,828,562 A | 5/1989 | Kenna |
| 4,870,957 A | 10/1989 | Goble et al. |
| 4,955,910 A | 9/1990 | Bolesky |
| 4,957,498 A | 9/1990 | Caspari et al. |
| 5,004,474 A | 4/1991 | Fronk et al. |
| 5,037,422 A | 8/1991 | Hayhurst et al. |
| 5,085,661 A | 2/1992 | Moss |
| 5,139,520 A | 8/1992 | Rosenberg |
| 5,161,916 A | 11/1992 | White et al. |
| 5,176,709 A | 1/1993 | Branemark |
| 5,188,636 A | 2/1993 | Fedotov |

(Continued)

FOREIGN PATENT DOCUMENTS

CA 2235354 A1 10/1999

(Continued)

OTHER PUBLICATIONS

Caborn et al., A Biomechanical Comparison of Initial Soft Tissue Tibial Fixation Devices: The Intrafix Versus a Tapered 35-mm Bioabsorbable Interference Screw, The American Journal of Sports Medicine, 2004, vol. 32, No. 4.

(Continued)

*Primary Examiner* — Bruce E Snow
(74) *Attorney, Agent, or Firm* — Stout, Uxa, Buyan & Mullins, LLP; Donald E. Stout

(57) ABSTRACT

An anterior cruciate ligament (ACL) surgical repair technique involves the use of a single femoral and tibial tunnel and an implant that separates and positions two distinct bundles. This allows for the surgeon to create a more anatomic reconstruction with a procedure that is less technically demanding, can be performed using a transtibial or anteromedial approach, minimizes tunnel widening, and decreases operative time. The result is a strong fixation option for soft tissue grafts, with circumferential graft compression at the aperture, high pull-out strength, and ease of use. The graft bundles are positioned in a more anatomic orientation through the above noted single femoral and tibial tunnel.

22 Claims, 6 Drawing Sheets

U.S. PATENT DOCUMENTS

| | | |
|---|---|---|
| 5,211,647 A | 5/1993 | Schmieding |
| 5,234,430 A | 8/1993 | Huebner |
| 5,236,445 A | 8/1993 | Hayhurst et al. |
| 5,258,016 A | 11/1993 | DiPoto et al. |
| 5,268,001 A | 12/1993 | Nicholson et al. |
| 5,281,237 A | 1/1994 | Gimpelson |
| 5,320,626 A | 6/1994 | Schmieding |
| 5,336,240 A | 8/1994 | Metzler et al. |
| 5,350,383 A | 9/1994 | Schmieding et al. |
| 5,354,298 A | 10/1994 | Lee et al. |
| 5,356,435 A | 10/1994 | Thein |
| 5,374,269 A | 12/1994 | Rosenberg |
| 5,383,878 A | 1/1995 | Roger et al. |
| 5,411,523 A | 5/1995 | Goble |
| 5,431,651 A | 7/1995 | Goble |
| 5,431,666 A | 7/1995 | Sauer et al. |
| 5,439,467 A | 8/1995 | Benderev et al. |
| 5,456,685 A | 10/1995 | Huebner |
| 5,464,427 A | 11/1995 | Curtis et al. |
| 5,466,237 A | 11/1995 | Byrd et al. |
| 5,474,555 A | 12/1995 | Puno et al. |
| 5,480,403 A | 1/1996 | Lee et al. |
| 5,486,197 A | 1/1996 | Le et al. |
| 5,507,750 A | 4/1996 | Goble et al. |
| 5,571,104 A | 11/1996 | Li |
| 5,571,184 A | 11/1996 | DeSatnick |
| 5,575,819 A | 11/1996 | Amis |
| 5,601,562 A | 2/1997 | Wolf et al. |
| 5,603,716 A | 2/1997 | Morgan et al. |
| 5,618,314 A | 4/1997 | Harwin et al. |
| 5,632,748 A | 5/1997 | Beck, Jr. et al. |
| 5,645,589 A | 7/1997 | Li |
| 5,702,215 A | 12/1997 | Li |
| 5,702,397 A | 12/1997 | Goble et al. |
| 5,707,395 A | 1/1998 | Li |
| 5,713,903 A | 2/1998 | Sander et al. |
| 5,718,706 A | 2/1998 | Roger |
| 5,725,529 A | 3/1998 | Nicholson et al. |
| 5,725,541 A | 3/1998 | Anspach, III et al. |
| 5,728,136 A | 3/1998 | Thal |
| 5,741,300 A | 4/1998 | Li |
| 5,743,912 A | 4/1998 | Lahille et al. |
| 5,769,894 A | 6/1998 | Ferragamo |
| 5,782,865 A | 7/1998 | Grotz |
| 5,814,073 A | 9/1998 | Bonutti |
| 5,845,645 A | 12/1998 | Bonutti |
| 5,846,254 A | 12/1998 | Schulze et al. |
| 5,871,504 A | 2/1999 | Eaton et al. |
| 5,899,938 A | 5/1999 | Sklar et al. |
| 5,902,303 A | 5/1999 | Eckhof et al. |
| 5,911,721 A | 6/1999 | Nicholson et al. |
| RE36,289 E | 8/1999 | Le et al. |
| 5,931,869 A | 8/1999 | Boucher et al. |
| 5,935,129 A | 8/1999 | McDevitt et al. |
| 5,941,901 A | 8/1999 | Egan |
| 5,957,953 A | 9/1999 | DePoto et al. |
| 5,961,520 A | 10/1999 | Beck, Jr. et al. |
| 5,964,764 A | 10/1999 | West, Jr. et al. |
| 5,968,078 A | 10/1999 | Grotz |
| 5,993,459 A | 11/1999 | Larsen et al. |
| 6,017,346 A | 1/2000 | Grotz |
| 6,086,608 A | 7/2000 | Ek et al. |
| 6,099,530 A | 8/2000 | Simonian et al. |
| 6,113,609 A | 9/2000 | Adams |
| 6,117,173 A | 9/2000 | Taddia et al. |
| 6,132,433 A | 10/2000 | Whelan |
| 6,146,406 A | 11/2000 | Shluzas et al. |
| 6,152,928 A | 11/2000 | Wenstrom, Jr. |
| 6,179,840 B1 | 1/2001 | Bowman |
| 6,187,008 B1 | 2/2001 | Hamman |
| 6,190,411 B1 | 2/2001 | Lo |
| 6,214,007 B1 | 4/2001 | Anderson |
| 6,221,107 B1 | 4/2001 | Steiner et al. |
| 6,325,804 B1 | 12/2001 | Wenstrom, Jr. et al. |
| 6,328,758 B1 | 12/2001 | Tornier et al. |
| 6,355,066 B1 | 3/2002 | Kim |
| 6,379,361 B1 | 4/2002 | Beck, Jr. et al. |
| 6,387,129 B2 | 5/2002 | Rieser et al. |
| 6,461,373 B2 | 10/2002 | Wyman et al. |
| 6,482,210 B1 | 11/2002 | Skiba et al. |
| 6,517,579 B1 | 2/2003 | Paulos et al. |
| 6,533,795 B1 | 3/2003 | Tran et al. |
| 6,533,816 B2 | 3/2003 | Sklar |
| 6,551,330 B1 | 4/2003 | Bain et al. |
| 6,554,862 B2 | 4/2003 | Hays et al. |
| 6,562,071 B2 | 5/2003 | Jarvinen |
| 6,616,694 B1 * | 9/2003 | Hart .................... 623/13.14 |
| 6,623,524 B2 | 9/2003 | Schmieding |
| 6,632,245 B2 | 10/2003 | Kim |
| 6,648,890 B2 | 11/2003 | Culbert et al. |
| 6,656,183 B2 | 12/2003 | Colleran et al. |
| 6,685,706 B2 | 2/2004 | Padget et al. |
| 6,716,234 B2 | 4/2004 | Grafton et al. |
| 6,730,124 B2 | 5/2004 | Steiner |
| 6,736,829 B1 | 5/2004 | Li et al. |
| 6,736,847 B2 | 5/2004 | Seyr et al. |
| 6,752,831 B2 | 6/2004 | Sybert et al. |
| 6,770,073 B2 | 8/2004 | McDevitt et al. |
| 6,770,084 B1 | 8/2004 | Bain et al. |
| 6,780,188 B2 | 8/2004 | Clark et al. |
| 6,796,977 B2 | 9/2004 | Yap et al. |
| 6,802,862 B1 | 10/2004 | Roger et al. |
| 6,833,005 B1 | 12/2004 | Mantas et al. |
| 6,887,271 B2 | 5/2005 | Justin et al. |
| 6,890,354 B2 | 5/2005 | Steiner et al. |
| 6,932,841 B2 | 8/2005 | Sklar et al. |
| 6,939,379 B2 | 9/2005 | Sklar |
| 6,942,666 B2 | 9/2005 | Overaker et al. |
| 6,942,668 B2 | 9/2005 | Padget et al. |
| 6,986,781 B2 | 1/2006 | Smith |
| 7,008,451 B2 | 3/2006 | Justin et al. |
| 7,037,324 B2 | 5/2006 | Martinek |
| 7,063,724 B2 * | 6/2006 | Re et al. .................... 623/13.14 |
| 7,083,638 B2 | 8/2006 | Foerster |
| 7,147,651 B2 | 12/2006 | Morrison et al. |
| 7,201,754 B2 | 4/2007 | Stewart et al. |
| 7,270,666 B2 * | 9/2007 | Lombardo et al. ............. 606/308 |
| 7,309,355 B2 | 12/2007 | Donnelly et al. |
| 7,326,247 B2 | 2/2008 | Schmieding et al. |
| 7,556,629 B2 | 7/2009 | Von Hoffmann et al. |
| 7,556,640 B2 | 7/2009 | Foerster |
| 2002/0040241 A1 * | 4/2002 | Jarvinen .................... 623/13.14 |
| 2002/0120280 A1 | 8/2002 | Wotton, III |
| 2002/0165611 A1 | 11/2002 | Enzerink et al. |
| 2003/0065391 A1 | 4/2003 | Re et al. |
| 2003/0083662 A1 | 5/2003 | Middleton |
| 2003/0109900 A1 | 6/2003 | Martinek |
| 2003/0135274 A1 | 7/2003 | Hays et al. |
| 2003/0199877 A1 | 10/2003 | Steiger et al. |
| 2003/0204204 A1 | 10/2003 | Bonutti |
| 2004/0024456 A1 | 2/2004 | Brown, Jr. et al. |
| 2004/0068267 A1 | 4/2004 | Harvie et al. |
| 2004/0097943 A1 | 5/2004 | Hart |
| 2004/0098050 A1 | 5/2004 | Foerster et al. |
| 2004/0098052 A1 | 5/2004 | West, Jr. et al. |
| 2004/0153153 A1 | 8/2004 | Elson et al. |
| 2004/0180308 A1 | 9/2004 | Ebi et al. |
| 2004/0181240 A1 | 9/2004 | Tseng et al. |
| 2004/0199165 A1 | 10/2004 | Culbert et al. |
| 2004/0230194 A1 | 11/2004 | Urbanski et al. |
| 2004/0237362 A1 | 12/2004 | O'Connell |
| 2004/0267362 A1 | 12/2004 | Hwang et al. |
| 2005/0033289 A1 | 2/2005 | Warren et al. |
| 2005/0251260 A1 | 11/2005 | Gerber et al. |
| 2006/0095131 A1 | 5/2006 | Justin et al. |
| 2006/0155287 A1 | 7/2006 | Montgomery et al. |
| 2008/0119929 A1 | 5/2008 | Schmieding et al. |
| 2011/0040380 A1 * | 2/2011 | Schmieding et al. ...... 623/13.14 |

FOREIGN PATENT DOCUMENTS

| | | |
|---|---|---|
| EP | 0232049 B1 | 3/1990 |
| EP | 0528573 A1 | 8/1992 |
| EP | 0688185 A1 | 2/1993 |
| EP | 1033115 A2 | 9/2000 |
| EP | 0762850 B1 | 2/2004 |
| EP | 0739185 B1 | 9/2004 |
| EP | 1011535 B1 | 12/2005 |

| FR | 2696925 | A1 | 4/1994 |
| JP | 10155820 | A | 6/1998 |
| WO | 8809157 | | 12/1988 |
| WO | 9216167 | A1 | 10/1992 |
| WO | 9515726 | A1 | 6/1995 |
| WO | 9812991 | A1 | 4/1998 |
| WO | 9818409 | | 5/1998 |
| WO | 0130253 | A1 | 5/2001 |
| WO | 02085256 | A1 | 10/2002 |

OTHER PUBLICATIONS

Charlton et al., Clinical Outcome of Anterior Cruciate Ligament Reconstruction with Quadrupled Hamstring Tendon Graft and Bioabsorbable Interference Screw Fixation, The American Journal of Sports Medicine, 2003, pp. 518-521, vol. 31, No. 4, Kerlan-Jobe Orthopaedic Clinic, Los Angeles.

Morgan et al., Anatomic Graft Fixation Using a Retrograde Biointerference Screw for Endoscopic Anterior Cruciate Ligament Reconstruction: Single-Bundle and 2-Bundle Techniques, Techniques in Orthopaedics, 2005, pp. 297-302, vol. 20, No. 3, Lippincott Williams & Wilkins, Inc., Philadelphia.

Robbe et al., Graft Fixation Alternatives in Anterior Cruciate Ligament Reconstruction, Spring 2002, pp. 21-28, vol. 15, Orthopaedic Surgery Department, University of Kentucky School of Medicine, Lexington, KY, U.S.A.

Scheffle et al., Biomechanical Comparison of Hamstring and Patellar Tendon Graft Anterior Cruciate Ligament Reconstruction Techniques: The Impact of Fixation Level and Fixation Method Under Cyclic Loading, Arthroscopy: The Journal of Arthroscopic and Related Surgery, Mar. 2002, pp. 304-315, vol. 18, No. 3, Arthroscopy Association of North America.

Simonian et al., Interference Screw Position and Hamstring Graft Location of Anterior Cruciate Ligament Reconstruction, The Journal of Arthroscopic and Related Surgery, Jul.-Aug. 1998, pp. 459-464, vol. 14, No. 5, The New York Hospital-Cornell University Medical College, New York, U.S.A.

Wolf, Eugene M., Hamstring Anterior Cruciate Ligament Reconstruction using Fermoral Cross-pin Fixation Operative Techniques in Sports Medicine, Oct. 1999, pp. 241-222, vol. 7, No. 4, W.B. Saunders Company, San Francisco, U.S.A.

A Biomechanical Comparison of Femoral RetroScrew Placement in a Porcine Model, Arthrex Research and Development, 2007, Arthex, Inc.

Scope This Out: A Technical Pearls Newsletter for Arthroscopists, Fall 1999, vol. 1, No. 3, Arthrex, Inc, U.S.A.

Scope This Out: A Technical Pearls Newsletter for Arthroscopists, Summer 2001, vol. 3, No. 2, Arthrex, Inc, U.S.A.

Scope This Out: A Technical Pearls Newsletter for Arthroscopists, Summer 2002, vol. 4, No. 2, Arthrex, Inc, U.S.A.

Scope This Out: A Technical Pearls Newsletter for Arthroscopists, Summer 2002, vol. 5, No. 2, Arthrex, Inc, U.S.A.

* cited by examiner

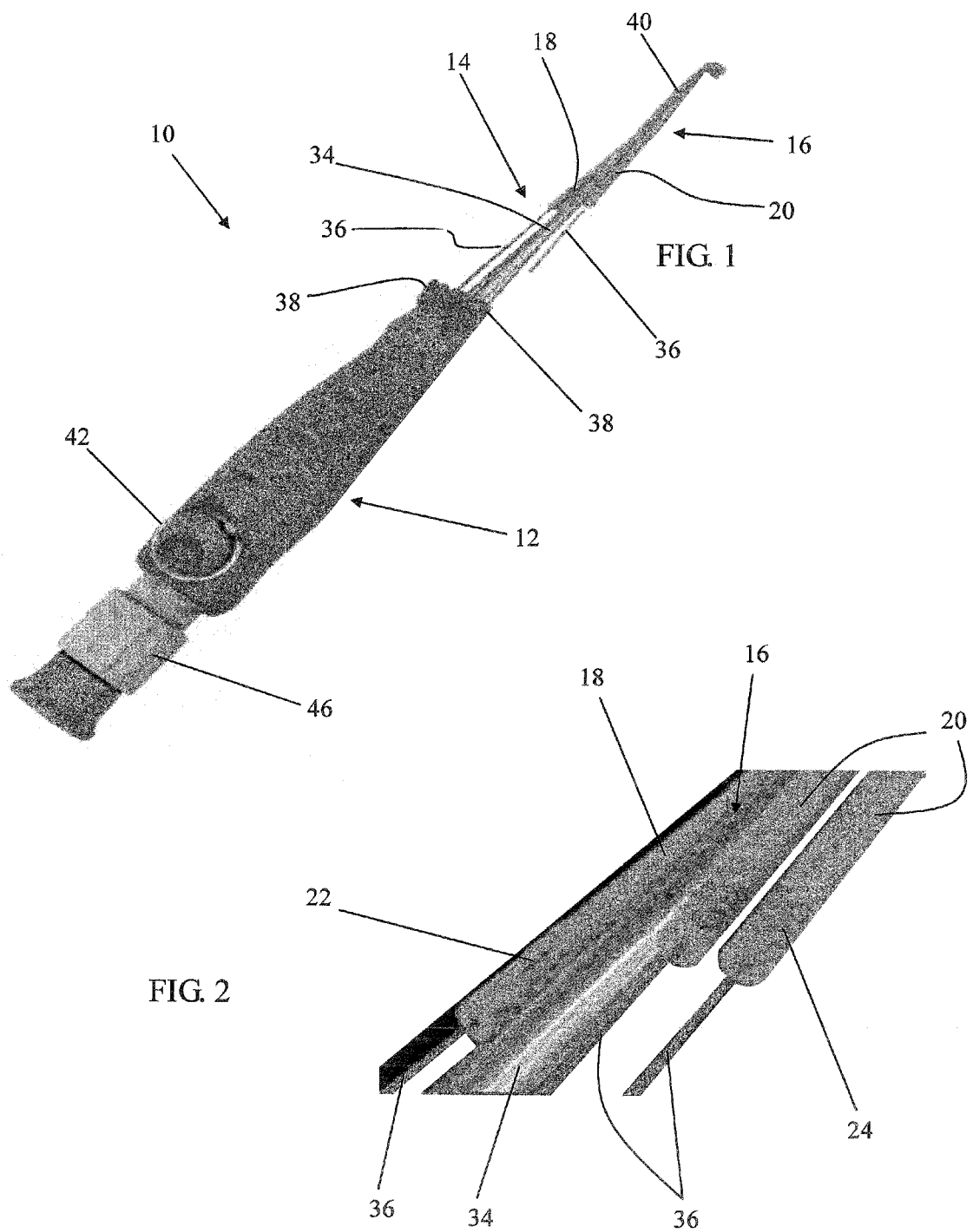

FIG. 3
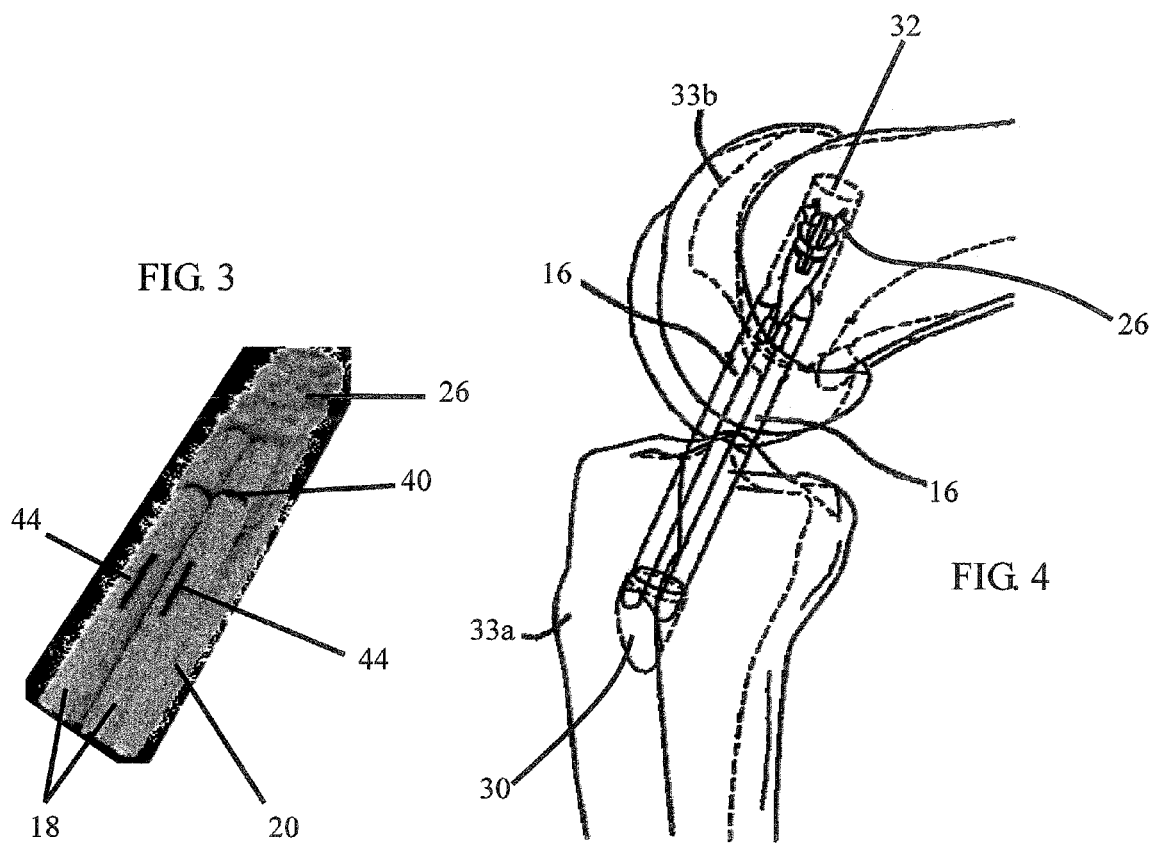
FIG. 4
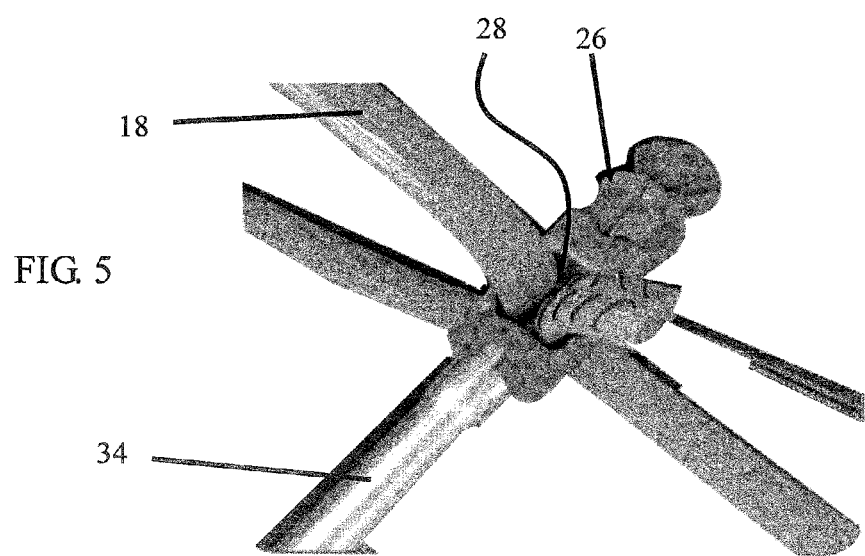
FIG. 5

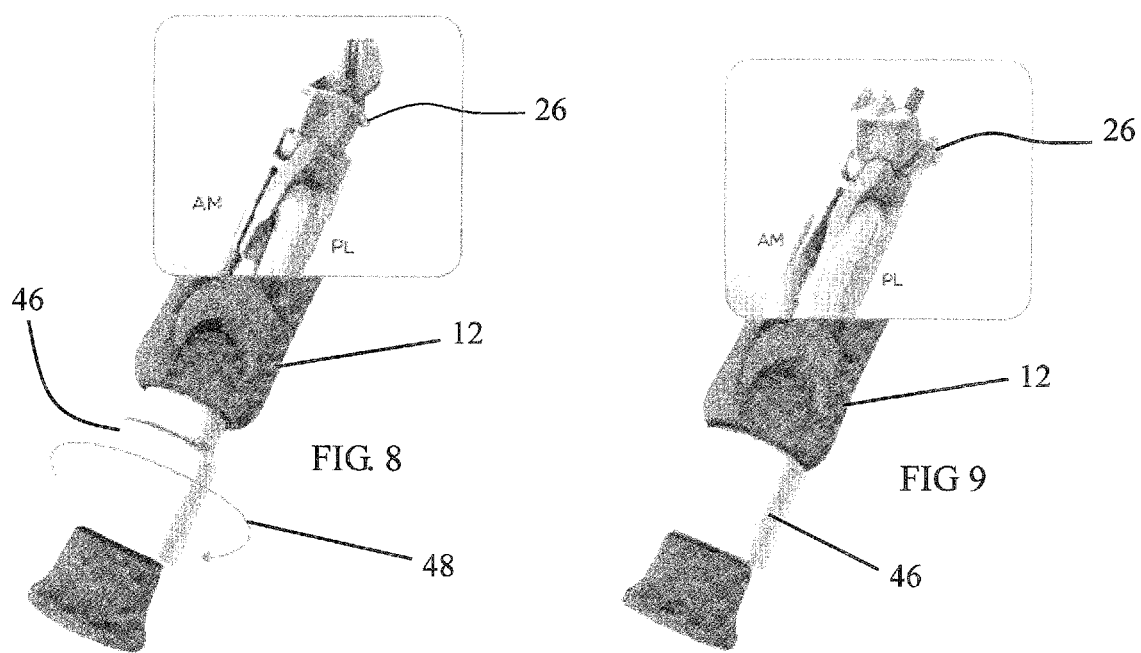
FIG. 8
FIG 9
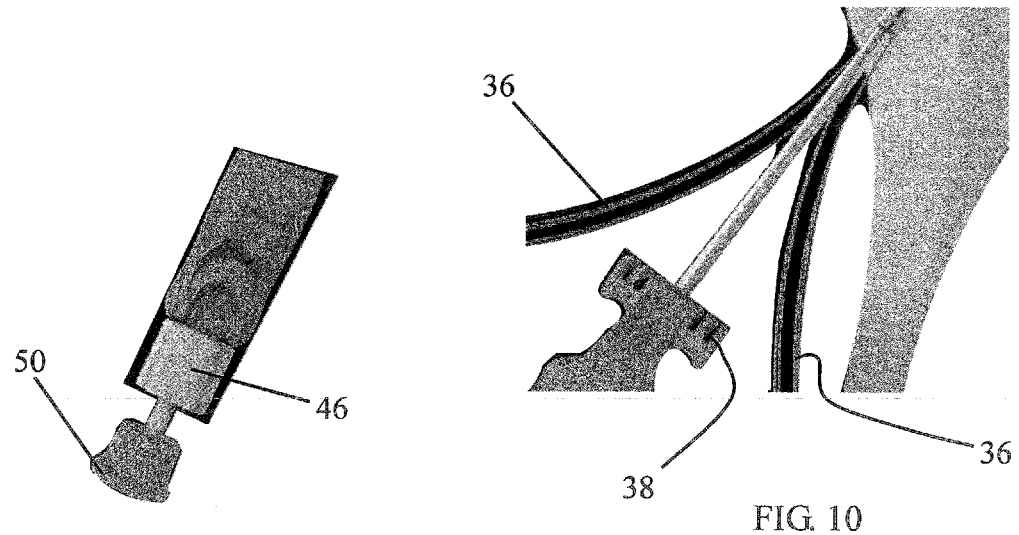
FIG. 11
FIG. 10

METHOD FOR SURGICALLY REPAIRING A DAMAGED LIGAMENT

This application claims the benefit under 35 U.S.C. 119(e) of the filing date of Provisional U.S. Application Ser. No. 61/158,994, entitled Anterior Cruciate Ligament Surgical Reconstruction Technique, filed on Mar. 10, 2009 and of the filing date of Provisional U.S. Application Ser. No. 61/158,999, also entitled Anterior Cruciate Ligament Surgical Reconstruction Technique, filed on Mar. 10, 2009.

This application is also related to U.S. application Ser. No. 11/281,566 entitled Devices, Systems, and Methods for Material Fixation, filed on Nov. 18, 2005 and now issued as U.S. Pat. No. 7,651,528, to co-pending U.S. application Ser. No. 11/725,981, entitled Devices, Systems, and Methods for Material Fixation, filed on Mar. 20, 2007, to co-pending U.S. application Ser. No. 11/923,526, entitled Methods and Systems for Material Fixation, filed on Oct. 24, 2007, to co-pending U.S. application Ser. No. 12/437,020, entitled Manual Soft Tissue Tensioning Systems and Methods, filed on May 7, 2009, to co-pending U.S. application Ser. No. 12/437,007, entitled Inserter for Soft Tissue or Bone-to-Bone Fixation Device and Methods, filed on May 7, 2009, and to co-pending U.S. application Ser. No. 12/634,581, entitled Devices, Systems, and Methods for Material Fixation, filed on Dec. 9, 2009.

All of the above prior applications are commonly owned and herein expressly incorporated by reference, in their entirety.

BACKGROUND OF THE INVENTION

The present invention relates generally to devices, systems and methods for material fixation. More specifically, the present invention relates to techniques that can be used to firmly hold a soft tissue or graft against bone tissue within a bone tunnel.

It is known that the anterior cruciate ligament (ACL) is comprised of two bundles, the anteromedial (AM) bundle and the posterolateral (PL) bundle. However, the traditional transtibial ACL reconstruction re-creates only the AM bundle, and recent data has shown that this may not restore normal rotational knee kinematics. In order to address this deficiency in rotational stability, surgeons have developed techniques to reconstruct both the AM and PL bundles of the ACL, comparing the double bundle reconstruction. These techniques, which require the to placement of two tibial and two femoral tunnels, increase the complexity of the operation, and this may result in increased complications and compromise revision surgery. In addition, the size of the tibial footprint may be prohibitively small in some patients, making it difficult to create two anatomic tunnels.

What is needed, therefore, are improved methods which do not require the creation of multiple tibial and/or femoral tunnels to achieve placement of a double bundle tendon graft.

SUMMARY OF THE INVENTION

The present invention comprises techniques which utilize a new implant system to reconstruct the ACL. The inventive techniques have been characterized as a "single-tunnel, double-bundle ACL reconstruction". This technique involves the use of a single femoral and tibial tunnel and an implant that separates and positions two distinct bundles. This allows for the surgeon to create a more anatomic reconstruction with a procedure that is less technically demanding, can be performed using a transtibial or anteromedial approach, minimizes tunnel widening, and decreases operative time. The result is a strong fixation option for soft tissue grafts, with circumferential graft compression at the aperture, high pull-out strength, and ease of use. The graft bundles are positioned in a more anatomic orientation through the above noted single femoral and tibial tunnel.

More particularly, there is described a method for repairing a damaged ligament surgically, which comprises a step of preparing a ligament graft to be inserted in place of the damaged ligament, wherein the graft comprises an anteromedial (AM) bundle having a plurality of graft strands and a posterolateral (PL) bundle having a plurality of graft strands. The preparing step further includes a step of securing the end of each graft strand of both bundles using suture, and a step of doubling the graft over itself. This suture securing step preferably includes stitching the ends of each graft strand using a whip stitch. Another innovative feature of the invention is the preferred usage of a first suture color to secure the graft strands of the AM bundle and a second different suture color to secure the graft strands of the PL bundle.

A femoral implant, which comprises movable portions which may be deployed to expand outwardly to engage adjacent bone, is selected to have a size suitably compatible to the size of the prepared ligament graft. A tibial tunnel and a femoral socket are created, using well known prior art methods, for receiving the ligament graft. Advantageously, unlike in prior techniques for attempting to utilize double bundle grafts in a single tunnel approach, no additional steps of widening the tibial tunnel or femoral socket are required to accommodate either the bulk of the graft bundles or interference fixation devices are required.

Additional method steps include securing the graft strand bundles to the femoral implant so that they extend proximally from both sides of the implant, wherein the AM bundle extends along one side of the implant and the PL bundle extends along an opposing side of the implant, and securing ends of the suture used to secure the graft bundles to an insertion device in a manner as to ensure optimal anatomical placement of the AM and PL graft bundles. The femoral implant is inserted through the tibial tunnel and into the femoral socket to a desired depth, following which, the movable portions of the femoral implant are deployed to expand outwardly into adjacent bone. The suture securing ends are disengaged from the insertion device, the insertion device is released from the femoral implant and proximally withdrawn from the tibial tunnel. Then, the graft bundles are tensioned, and their proper positioning in the knee is ensured.

Advantageously, neither the femoral implant nor the tibial implant utilize interference fixation to secure the graft. The graft strand bundles are secured to the femoral implant by inserting them through an aperture extending through the implant. In a preferred approach, the step of securing the ends of the suture to an insertion device comprises securing the ends of the suture extending from the AM bundle to one side of the insertion device and the ends of the suture extending from the PL bundle the an opposing side of the insertion device. The step of securing the ends of the suture to the insertion device comprises wrapping the suture about suture cleats disposed on the insertion device.

Another advantageous feature of the inventive methods comprises a step of making a horizontal mark on the tendon bundles at an edge of the femoral implant to serve as a depth indicator. Marks are also made on the graft strands that represent the AM bundle on the both the implant end and the sutured end to assist in identification of the respective AM and PL bundles during the procedure.

Before the femoral implant is deployed, the grafts representing the AM bundle are positioned in a poster-superior position and the grafts representing the PL bundle in an antero-inferior position prior to deploying the femoral implant.

The step of tensioning the graft bundles preferably further comprises a step of securing the suture ends extending from the AM bundle to one side of a tensioning device and a further step of securing the suture ends from the PL bundle to an opposing side of the tensioning device, in order to ensure that equal tension is applied to each graft.

The inventive method additionally comprises a step of inserting and deploying a tibial anchor for securing the graft bundles in place within the tibial tunnel.

The invention, together with additional features and advantages thereof, may best be understood by reference to the following description taken in conjunction with the accompanying illustrative drawing.

BRIEF DESCRIPTION OF THE DRAWINGS

FIG. 1 is an isometric view of an insertion device for inserting and deploying a femoral implant;

FIG. 2 is an enlarged view of a portion of the distal end of the inserter of FIG. 1, showing the graft bundles to be anchored using the inventive techniques;

FIG. 3 is an enlarged view of a different portion of the distal end of the inserter of FIG. 1, again showing the graft bundles to be anchored using the inventive techniques;

FIG. 4 is a representation of the implant system as described herein as it is installed in a human knee;

FIG. 5 is a view illustrating soft tissue grafts as prepared using the techniques of the present invention, after they have been passed through the orifices of the femoral implant;

FIG. 8 is an illustration of a step of deploying the implant under the inventive technique;

FIG. 9 is an illustration of a step subsequent to the step shown in FIG. 8;

FIG. 10 is an illustration showing the sutures disengaged from the suture cleats;

FIG. 11 is a view of the handle portion of the inserter of FIG. 7, showing a releasing step for releasing the inserter from the implant;

DETAILED DESCRIPTION OF THE INVENTION

Figure 6:
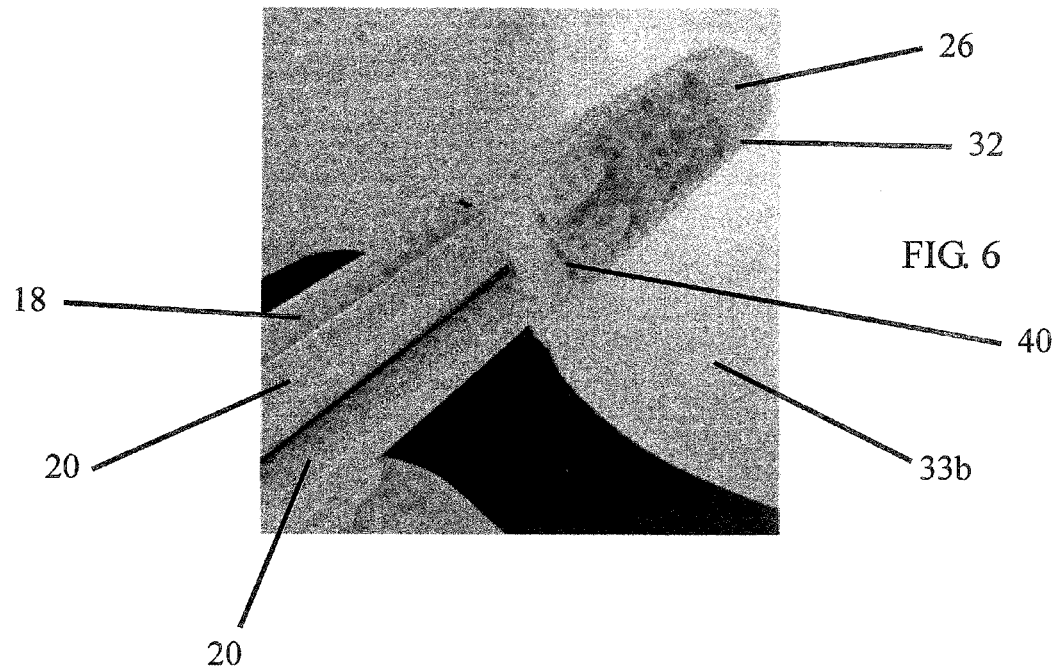
FIG. 6 is an enlarged illustration of the femoral implant and graft as implanted, with the knee in a flexed orientation.

The present inventive technique is indicated for primary and revision reconstruction of ACL deficient patients. The procedure should be considered for any patient with a pronounced pivot shift, and therefore, rotational instability. The inventive ACL reconstruction techniques afford surgeons a strong fixation option for soft tissue grafts, with circumferential graft compression at the aperture, high pull-out strength, and ease of use. The graft bundles are positioned in a more anatomic orientation through a single femoral and tibial tunnel.

Arthroscopy and Preparation

In accordance with the inventive techniques, the patient is positioned supine on the operating table in the ACL position preferred by the surgeon. A diagnostic arthroscopy is performed and concomitant pathology is addressed. Diagnosis of ACL rupture is confirmed and the ACL remnant is derided. The center of the both the tibial and femoral footprints of the ACL are identified and marked with a thermal device prior to complete removal. These locations will serve as the center for the femoral socket and tibial tunnel.

Graft Preparation

A hamstring autograft or allograft is recommended. Alternatively, if tibialis allograft (anterior or posterior) is used, one half of the graft must be divided into two segments, each with an approximate width of 6 mm. In the illustrated example, graft preparation is completed using the Gracilis and Semitendinosis tendons.

Referring particularly to FIGS. 1-6, in FIG. 1 there is shown an insertion device 10 which comprises a handle portion 12 and a distal end portion 14. A graft 16 is disposed about the distal end 14 of the device 10. The graft 16 comprises an AM bundle 18 and a PL bundle 20. Both ends of both graft strands are secured, preferably with a #2 non-absorbable suture in a whip-stitch fashion, as shown at 22 and 24, respectively. In a preferred approach, different colored sutures are used to distinguish between the AM and PL bundles. For example, one end of the Semitendinosis Graft is stitched with a blue suture, and the other end with a green suture. The same process is completed with the Gracilis Graft.

Once the graft strands are stitched, the graft is doubled over itself and measured with a sizing guide, such as a graft sizing block (not shown), trough which the graft bundles are pulled. Using a graft sizing block, a diameter is selected through which the graft bundle fits tightly, but still passes through. An appropriately sized femoral implant 26 is then selected, and each graft strand is mounted onto the femoral implant 26, by inserting the strands through the implant aperture 28 as shown particularly in FIG. 5.

Tibial Tunnel Placement

A tibial tunnel 30 and femoral socket 32 (FIG. 4) are created in the tibia 33a and femur 33b, respectively, in the usual fashion. A particular advantage of the present invention, in contrast to prior approaches, is that little or no modification, such as widening or notching, of the otherwise usual tunnels need be performed. Thus, the tibial tunnel 30 is placed in the center of the tibial footprint. This is medial to the posterior aspect of the anterior horn of the lateral meniscus. The guide pin for the tibial tunnel is placed immediately anterior to the MCL with the tibial guide set at 50 degrees, at a minimum of 3 cm distal to the joint. This medial starting point creates a more horizontal tibial tunnel, allowing placement of a femoral socket lower down the notch wall. The guide pin is drilled from this point to the center of the ACL tibial footprint, on the medial third of the intercondylar plateau, in line with the posterior border of the anterior horn of the lateral meniscus. This guide pin is then over-drilled with the appropriate sized cannulated reamer, typically 9 or 10 mm, as previously determined by the size of the graft.

Femoral Socket Placement

The femoral socket 32 is positioned in the center of the femoral footprint, low on the femoral notch (two o'clock in a left knee, ten o'clock position in a right knee). This location is typically accessible with an ACL over-the-top guide through the tibial tunnel. Alternatively, if this point is not accessible through the tibial tunnel, a low antero-medial portal is employed. The guide pin for the femoral fixation device should be inserted to the cortex of the femur. Depth marks on the guide pin indicate the length of the femoral tunnel. After insertion of the guide pin, the pin is over-reamed with the appropriately sized reamer, usually 9 or 10 mm, to a depth that permits femoral implant placement (minimum 30 mm).

Graft Placement and Fixation

The distal end portion 14 of the insertion device 10 comprises a shaft 34, to the distal end of which is secured the femoral implant 26, as shown in FIG. 5. The next step in the inventive procedure is to pass the prepared soft tissue double bundle grafts 16 through the orifice or aperture 28, as also shown in FIG. 5. Then, the sutures 36 of the prepared tendons 16 are wrapped around suture cleats 38 on the inserter handle portion 12 (FIG. 1). To achieve optimal anatomical placement of the bundles, it is preferred that the like-colored, sutured graft ends representing the AM bundle be wrapped on one suture cleat. The sutured ends representing the PL bundle are wrapped on the opposite suture cleat. A horizontal mark 40 (FIG. 1) is made on the tendon bundles at the inferior edge of the implant 26 to serve as the aperture depth indicator. By turning the inserter handle 12 over, with the safety pin 42 facing down, additional marks 44 (FIG. 3) are made on the grafts that represent the AM bundle at both the implant end and the sutured end. This helps with intra-articular and extra-articular identification of the bundles once inserted into the femoral tunnel.

The femoral fixation device 26 with the graft 16 properly positioned is inserted through the tibial tunnel 30 (or the AM portal if this was used to create the femoral tunnel) into the femoral socket 32. This insertion step is preferably done while holding the implant inserter handle portion 12 with the safety pin 42 in an upward facing orientation, and the insertion step continues until the implant is moved distally into the femoral socket to the marked depth location 40. This step is illustrated in FIG. 6. The device should be oriented so that one graft is positioned postero-superior (ten o'clock position in the left knee flexed to 90 degrees) and one graft is antero-inferior (four o'clock position in the left knee flexed to 90 degrees) to approximate anatomic orientation until the implant is seated. For the illustrated device, this is accomplished particularly, for the purpose of achieving optimal anatomic femoral placement of the graft bundles, by rotating the inserter, with the knee flexed to 90 degrees, until the marked grafts representing the AM bundle are placed in the postero-superior position and the PL bundles are placed in the antero-inferior position. Orientation of the suture cleats 38, located on the inserter handle 12, will be approximately 10 and 4 o'clock for a left knee.

Figure 7:
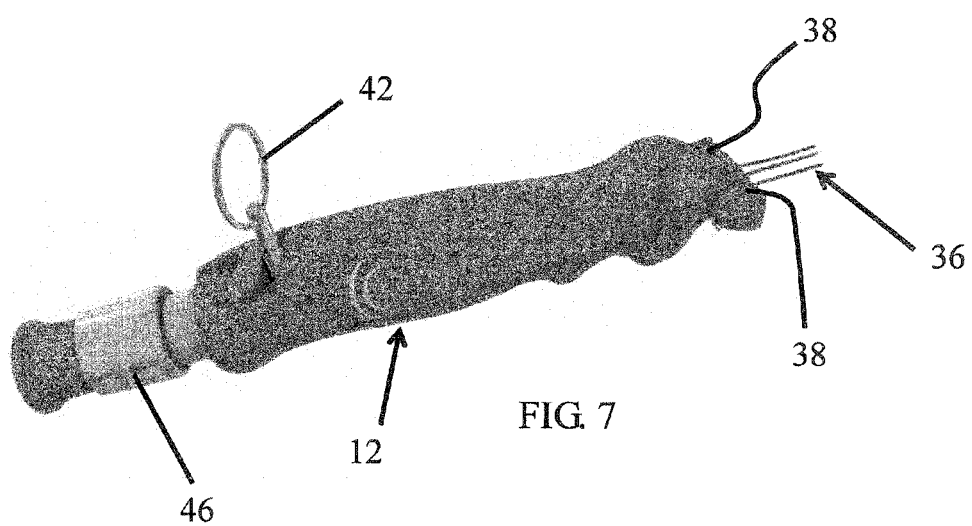
FIG. 7 is an isometric view of the handle portion of the inserter of FIG. 1.

The device is then deployed, providing for aperture femoral fixation. This is done by ensuring the implant is in proper position and the safety pin 42 is completely pulled out of the handle 12, by pulling upwardly (FIG. 7). The release of the safety pin 42 permits a deployment knob 46 to rotate.

With the inserter handle 12 held firmly in place, the implant deployment knob 46 may be rotated (FIG. 8) in the direction of arrow 48, clockwise, until the deployment knob can no longer be turned, advancing distally to the point that it comes into contact with the remaining portion of the inserter handle 12. This advanced position is shown in FIG. 9, wherein the femoral implant is fully deployed, to engage expanded portions of the implant, which have been moved outwardly during the deployment sequence, as shown, with adjacent bone.

Once the implant 26 is deployed, the sutures 36 are disengaged from the suture cleats 38, as shown in FIG. 10. The inserter 10 is then released from the implant 26 by pulling proximally an implant release knob 50 from the deployment knob 46, as illustrated in FIG. 11, and holding it in the retracted position. Next, the inserter handle 12 is drawn back. The inserter 12 is removed from the operative site and discarded.

Figure 12:
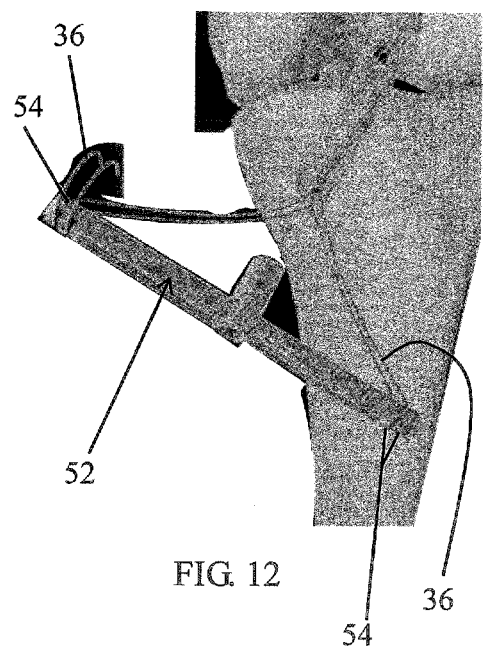
FIG. 12 is a view illustrating a first step in a sequence of orienting and tensioning the suture.

A tendon expander or suture tensioning device 52 is held in an orientation generally perpendicular to the tibial tunnel (FIG. 12), and the sutured ends 36 of the tendon bundles are wrapped around suture cleats 54 on either end of the tensioning device 52. This is done in such a way that the sutures are first inserted into lateral slits 56 (FIG. 13), and then wrapped around the vertical cleats 54. This procedure is disclosed more fully in U.S. application Ser. No. 12/487,020, already expressly incorporated herein by reference. By anchoring the AM and PL bundles to opposite sides of the tensioner, equal tension is applied to each graft using this convenient one-handed device.

Figure 14:
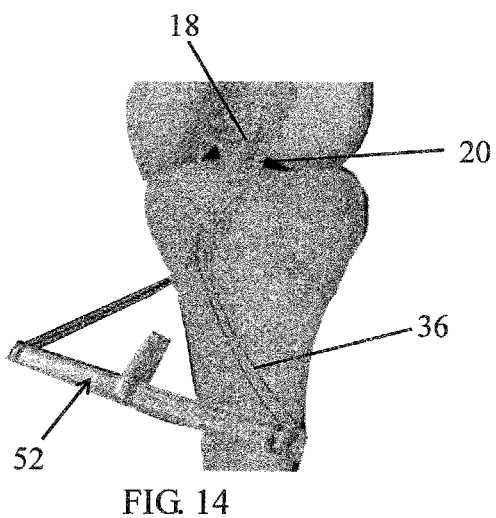
FIG. 14 is a view illustrating a third step in the sequence.
Figure 13:
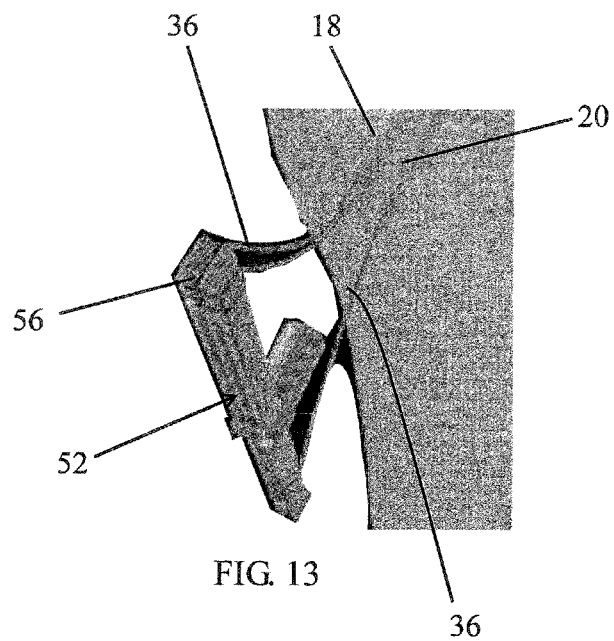
FIG. 13 is a view illustrating a second step in the sequence.
Figure 15:
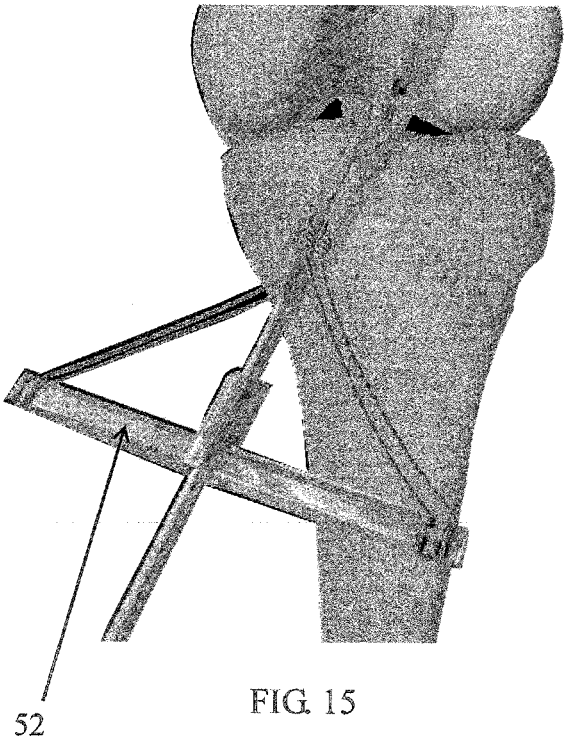
FIG. 15 is a view illustrating a fourth step in the sequence.

As shown sequentially in FIGS. 13-15, for proper orientation of the graft bundles at the tibial aperture, the tensioner 52 is positioned, as noted above, until the tendons representing the AM bundle are positioned in the anteromedial portion of the tunnel, and the PL bundle is positioned in the posterolateral portion. Rotation occurs by holding the T-handle of the tensioner, with visualization of the tibial footprint, so that one graft limb is positioned in the anteromedial portion of the tunnel and one in the posterolateral portion. This process of positioning the bundles can be facilitated by inserting a flat device, such as a Freer elevator, into the tibial tunnel between the bundles to rotate the graft at the internal aperture. Holding the bundles in the desired orientation, the knee is then cycled with tension applied to the graft.

Figure 16:
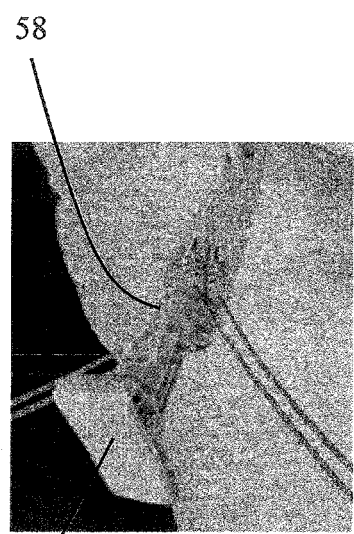
FIG. 16 is a view illustrating a step of inserting the tibial sheath into the knee.

Once this tensioning procedure has been completed, it is time to insert the tibial sheaths and screw, with the sheaths being oriented so that one bundle sits at the PL aspect of the tunnel and the other sits on the AM border. The knee is placed in full extension, and with the graft under tension, the tibial sheaths 58 are inserted into the tibial tunnel, between the tendon bundles, such that cortical engagement tabs 61 (FIGS. 18 and 19) on the sheaths are in the 9 o'clock position for a left knee and 3 o'clock for a right knee. The sheaths should be positioned so that the tabs 61 are fully seated against the tibia. Care is taken throughout this final procedure to maintain tension on the graft with the tensioner 52 to prevent loss of graft tension. At this point, the sheath inserter 60 (FIG. 16) is snapped off, disengaged from the sheaths, and discarded.

Figure 17:
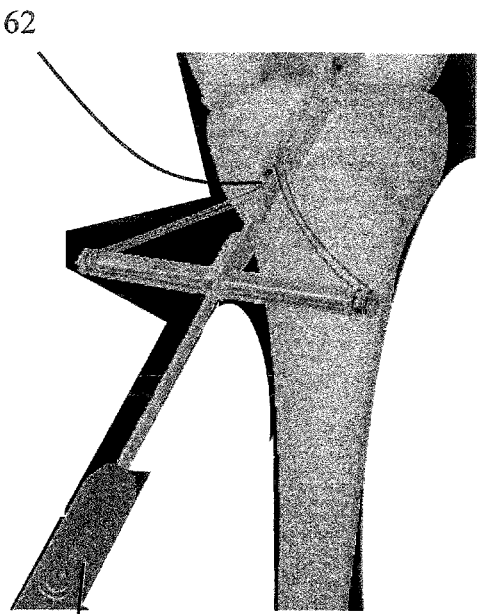
FIG. 17 is a view showing a step of inserting the tibial screw into the sheaths and tightening the screw.
Figure 18:
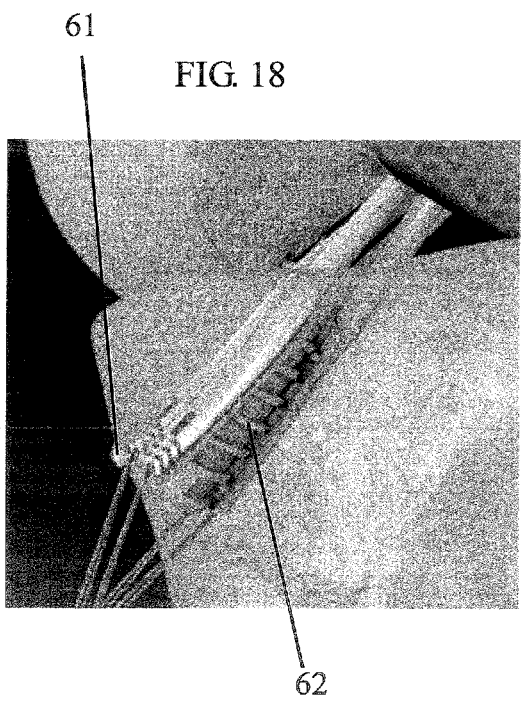
FIGS. 18 and 19 are views showing the installed tibial sheath.
Figure 19:
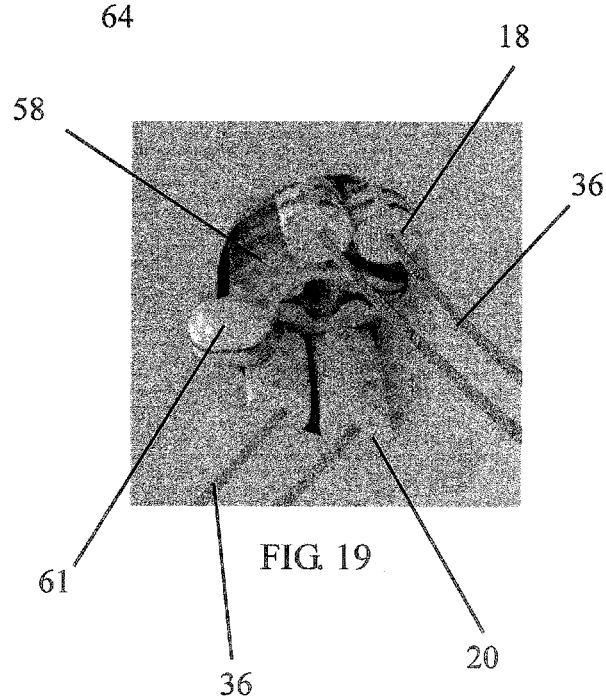

At this juncture, a tibial screw 62, selected to be of a size to match the diameter of the tibial tunnel, is securely placed onto a distal end of a tibial inserter 64 (FIG. 17). The screw and inserter are inserted into the tibial tunnel, through an aperture in the tensioning device 52, as shown in FIG. 17, so that the tibial screw is positioned in the center of the sheaths, with the tip of the screw engaging the sheaths. The inserter 64 is then turned clockwise until the screw head is flush with the superior rim of the cortical wall. Because tibial screw threads are designed to match those of the sheaths, excess torque is not needed to engage and insert the screw. As shown in FIGS. 18 and 19, once the tibial screw has been completely seated to the cortical wall, the inserter 64 is removed by pulling the handle straight back. The integrity of the repair is then checked, after which the excess suture 36 and tendon is trimmed flush with the tibial tunnel.

Accordingly, although exemplary embodiments of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method for repairing a damaged ligament surgically, comprising:
   preparing a ligament graft to be inserted in place of the damaged ligament, wherein the graft comprises an anteromedial (AM) bundle having a plurality of graft strands and a posterolateral (PL) bundle having a plurality of graft strands, the preparing step including a step of securing the end of each graft strand of both bundles using suture, and a step of doubling the graft over itself;
   selecting a femoral implant, which comprises movable portions which may be deployed to expand outwardly to engage adjacent bone, having a size suitable for the size of the prepared ligament graft;
   creating a tibial tunnel and a femoral socket for receiving the ligament graft;
   securing the graft strand bundles to the femoral implant so that they extend proximally from both sides of the implant, wherein the AM bundle extends along one side of the implant and the PL bundle extends along an opposing side of the implant, the securing step including using a first suture color to secure the graft strands of the AM bundle and using a second different suture color to secure the graft strands of the PL bundle;
   securing ends of the suture used to secure the graft bundles to an insertion device in a manner as to ensure optimal anatomical placement of the AM and PL graft bundles;
   inserting the femoral implant through the tibial tunnel and into the femoral socket to a desired depth;
   deploying the movable portions of the femoral implant to expand outwardly into adjacent bone;
   disengaging the suture securing ends from the insertion device;
   releasing the insertion device from the femoral implant and proximally withdrawing the insertion device from the tibial tunnel; and
   tensioning the graft bundles and ensuring their proper positioning in the knee.

2. The method as recited in claim 1, wherein the suture securing step includes stitching the ends of each graft strand using a whip stitch.

3. The method as recited in claim 1, wherein the creating step does not include a step of widening either the tibial tunnel or the femoral socket so that they are substantially wider in one radial direction than another.

4. The method as recited in claim 1, wherein the creating step does not include a step of creating notches in either the femoral socket or the tibial tunnel.

5. The method as recited in claim 1, wherein the graft strand bundles are secured to the femoral implant by inserting them through an aperture extending through the implant.

6. The method as recited in claim 1, wherein the step of securing the ends of the suture to an insertion device comprises securing the ends of the suture extending from the AM bundle to one side of the insertion device and the ends of the suture extending from the PL bundle the an opposing side of the insertion device.

7. The method as recited in claim 6, wherein the step of securing the ends of the suture to the insertion device comprises wrapping the suture about suture cleats disposed on the insertion device.

8. The method as recited in claim 1, and further comprising a step of making a horizontal mark on the tendon bundles at an edge of the femoral implant to serve as a depth indicator.

9. The method as recited in claim 1, and further comprising a step of positioning the grafts representing the AM bundle in a poster-superior position and the grafts representing the PL bundle in an antero-inferior position prior to deploying the femoral implant.

10. The method as recited in claim 1, wherein the step of tensioning the graft bundles further comprises a step of securing the suture ends extending from the AM bundle to one side of a tensioning device and a further step of securing the suture ends from the PL bundle to an opposing side of the tensioning device, in order to ensure that equal tension is applied to each graft.

11. The method as recited in claim 1, and further comprising a step of inserting and deploying a tibial anchor for securing the graft bundles in place within the tibial tunnel.

12. A method for repairing a damaged ligament surgically, comprising:
   preparing a ligament graft to be inserted in place of the damaged ligament, wherein the graft comprises an anteromedial (AM) bundle having a plurality of graft strands and a posterolateral (PL) bundle having a plurality of graft strands, the preparing step including a step of securing the end of each graft strand of both bundles using suture, and a step of doubling the graft over itself;
   selecting a femoral implant, which comprises movable portions which may be deployed to expand outwardly to engage adjacent bone, having a size suitable for the size of the prepared ligament graft;
   creating a tibial tunnel and a femoral socket for receiving the ligament graft;
   securing the graft strand bundles to the femoral implant so that they extend proximally from both sides of the implant, wherein the AM bundle extends along one side of the implant and the PL bundle extends along an opposing side of the implant;
   securing ends of the suture used to secure the graft bundles to an insertion device in a manner as to ensure optimal anatomical placement of the AM and PL graft bundles;
   inserting the femoral implant through the tibial tunnel and into the femoral socket to a desired depth;
   deploying the movable portions of the femoral implant to expand outwardly into adjacent bone;
   disengaging the suture securing ends from the insertion device;
   releasing the insertion device from the femoral implant and proximally withdrawing the insertion device from the tibial tunnel;
   tensioning the graft bundles and ensuring their proper positioning in the knee; and
   making marks on the graft strands that represent the AM bundle on the both the implant end and the sutured end to assist in identification of the respective AM and PL bundles during the procedure.

13. The method as recited in claim 12, wherein the suture securing step includes stitching the ends of each graft strand using a whip stitch.

14. The method as recited in claim 12, wherein the creating step does not include a step of widening either the tibial tunnel or the femoral socket so that they are substantially wider in one radial direction than another.

15. The method as recited in claim 12, wherein the creating step does not include a step of creating notches in either the femoral socket or the tibial tunnel.

16. The method as recited in claim 12, wherein the graft strand bundles are secured to the femoral implant by inserting them through an aperture extending through the implant.

17. The method as recited in claim 12, wherein the step of securing the ends of the suture to an insertion device comprises securing the ends of the suture extending from the AM bundle to one side of the insertion device and the ends of the suture extending from the PL bundle the an opposing side of the insertion device.

18. The method as recited in claim 17, wherein the step of securing the ends of the suture to the insertion device comprises wrapping the suture about suture cleats disposed on the insertion device.

19. The method as recited in claim 12, and further comprising a step of making a horizontal mark on the tendon bundles at an edge of the femoral implant to serve as a depth indicator.

20. The method as recited in claim 12, and further comprising a step of positioning the grafts representing the AM bundle in a poster-superior position and the grafts representing the PL bundle in an antero-inferior position prior to deploying the femoral implant.

21. The method as recited in claim 12, wherein the step of tensioning the graft bundles further comprises a step of securing the suture ends extending from the AM bundle to one side of a tensioning device and a further step of securing the suture ends from the PL bundle to an opposing side of the tensioning device, in order to ensure that equal tension is applied to each graft.

22. The method as recited in claim 12, and further comprising a step of inserting and deploying a tibial anchor for securing the graft bundles in place within the tibial tunnel.

* * * * *